(12) United States Patent
Schmidt et al.

(10) Patent No.: US 8,663,113 B2
(45) Date of Patent: Mar. 4, 2014

(54) METHOD FOR IMAGING A VOLUME OF TISSUE

(75) Inventors: Steven P Schmidt, Clinton Township, MI (US); Cuiping Li, Troy, MI (US); Olivier Roy, Royal Oak, MI (US); Ivana Jovanovic, Lausanne (CH)

(73) Assignee: Delphinus Medical Technologies, Inc., Plymouth, MI (US)

( * ) Notice: Subject to any disclaimer, the term of this patent is extended or adjusted under 35 U.S.C. 154(b) by 263 days.

(21) Appl. No.: 13/208,193

(22) Filed: Aug. 11, 2011

(65) Prior Publication Data

US 2013/0041260 A1 Feb. 14, 2013

(51) Int. Cl.
*A61B 8/00* (2006.01)

(52) U.S. Cl.
USPC ....................................................... 600/442

(58) Field of Classification Search
None
See application file for complete search history.

(56) References Cited

U.S. PATENT DOCUMENTS

| 2004/0122325 | A1 | 6/2004 | Chambers et al. |
| 2007/0282200 | A1 | 12/2007 | Johnson et al. |
| 2008/0058682 | A1 | 3/2008 | Azhari et al. |

OTHER PUBLICATIONS

Li et al., Comparison of ultrasound attenuation tomography methods for breast imaging, Medical Imaging 2008: Ultrasonic Imaging and Signal Processing, Proc. of SPIE vol. 6920, 692015-(1-9), 2008.*
Li et al., Breast Imaging Using Transmission Ultrasound: Reconstructing Tissue Parameters of Sound Speed and Attenuation, 2008 International Conference on BioMedical Engineering and Informatics, IEEE computer society, 708-712.*
Li et al., Refraction corrected transmission ultrasound computed tomography for application in breast imaging, Med. Phys. 37 (5), May 2010, 2233-2246.*
Walach et al., Local Tissue Attenuation Images Based on Pulsed-Echo Ultrasound Scans, IEEE Transactions on Biomedical Engineering, vol. 36. No. 2, Feb. 1989.*
Chang et al., Kirchhoff migration of ultrasonic images, Materials evaluation, V59, N3, 413-417, 2001.*
Klimes, Grid Travel-time Tracing: Second-order Method for the First Arrivals in Smooth Media, PAGEOPH, vol. 148, Nos. 3/4, 1996.*
Schmidt et al., "Modification of Kirchhoff migration with variable sound speed and attenuation for tomographic imaging of the breast," Proc. of SPIE vol. 7968, Mar. 25, 2011.

* cited by examiner

*Primary Examiner* — Long V. Le
*Assistant Examiner* — Bo J Peng
(74) *Attorney, Agent, or Firm* — Jeffrey Schox (57) ABSTRACT

A method for imaging a volume of tissue in a scan region, including: emitting, from transmitting transducers, acoustic waveforms toward the volume of tissue; detecting, with detecting transducers, a plurality acoustic signals derived from acoustic waveforms interacting with the volume of tissue; generating from the detected acoustic signals a plurality of variable attenuation maps, in which each variable attenuation map corresponds to acoustic signals detected by a respective detecting transducer and includes a plurality of variable attenuation coefficients mapped to the scan region; modifying at least a portion of the detected acoustic signals based on one or more variable attenuation maps; and generating a reflection rendering of the volume of tissue based on the modified acoustic signals.

22 Claims, 11 Drawing Sheets

METHOD FOR IMAGING A VOLUME OF TISSUE

TECHNICAL FIELD

This invention relates generally to the medical imaging field, and more specifically to an improved method for imaging a volume of tissue in the ultrasound medical imaging field.

BACKGROUND

Early detection of breast cancer and other types of cancer is typically an important factor in successful treatment. Ultrasound tomography is a promising imaging modality that has the potential to improve medical imaging of tissue for screening and diagnosis purposes compared to conventional imaging techniques. For instance, mammography is the current standard for breast screening, but involves ionizing radiation that precludes frequent imaging, and mammography has low sensitivity for detection of cancer in patients with dense breast tissue, which leads to a relatively high false negative rate. As another example, magnetic resonance imaging (MRI) is prohibitively expensive for routine and also has limited accessibility.

The basic principle of ultrasound involves emitting an acoustic wave or beam along a focused path from a source transmitter, and allowing the wave to scatter (e.g. in reflection, refraction, diffraction, transmission) from tissue or other boundaries in its path. The scattered wave returns to a surface of receiving elements, which is usually centered around and including the transmitter. The time of translation is converted into a depth distance by, multiplying the time by an assumed constant speed of sound in the media. The received signal is output to a graphical display for user interpretation.

However, current methods of ultrasonic imaging have some drawbacks and limitations. The assumption of a constant sound speed of propagation can cause angular displacement of objects due to refractions of the beam at boundary interfaces, and result in boundaries imaged closer than or further away from their actual positioning. Furthermore, to compensate for signal decay due to attenuation in tissue (energy loss due to scatter and energy absorption), conventional ultrasound systems incorporate automatic gain compensation (AGC) and/or time gain compensation (TGC) which allow a user to adjust signal compensation with respect to depth distance and provide a hardcoded gain to compensate for pre-supposed minimum signal decay. However, these compensations lead to another form of artifact caused by media of varying attenuation, which can degrade the image quality. If an object of attenuation lower than that assumed by the compensation techniques lies in the path of the beam, the resulting image includes a brightening of hyperechoic tissue behind the object. Similarly, if an object of attenuation higher than that assumed by the compensation techniques lies in the path of the beam, the resulting image includes a shadow of hypoechoic tissue behind the object.

Thus, there is a need in the ultrasound imaging field to create an improved method for imaging a volume of tissue. This invention provides such an improved method for imaging a volume of tissue.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
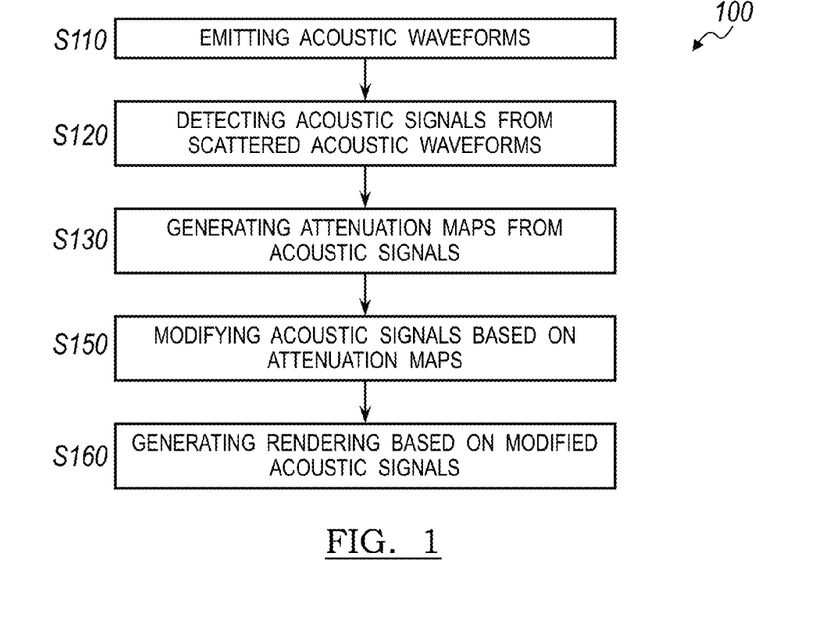
FIG. 1 is a schematic of the method of a preferred embodiment.

In a preferred embodiment, as shown in FIG. 1, the method 100 for imaging a volume of tissue in a scan region includes: emitting acoustic waveforms toward the volume of tissue S110; detecting, with detecting transducers, a plurality of acoustic signals S120 derived from acoustic waveforms interacting with the volume of tissue; generating, from the detected acoustic signals, a plurality of variable attenuation maps S130, in which each variable attenuation map corresponds to acoustic signals detected by a respective detecting transducer and includes a plurality of attenuation coefficients mapped to the scan region; modifying at least a portion of the detected acoustic signals based on one or more variable attenuation maps S150; and generating a reflection rendering of the volume of tissue based on the modified acoustic signals S160. The method 100 is preferably used to visually characterize tissue of a human breast, but may additionally and/or alternatively be used to characterize tissue of an arm, leg, other appendage, or any suitable volume of tissue in a human or other animal. In one embodiment, the method is used to detect cancer in a human or other animal. In another embodiment, the method is used to characterize the tissue to diagnose presence of cancer, assess its type and determine its extent (e.g., to determine whether a mass in the tissue is surgically removable), or to assess risk of cancer development (e.g., measuring breast tissue density). In yet another embodiment, the method is used to characterize and/or investigate particular aspects of the tissue, such as to determine whether a mass in the tissue is a tumor, cyst, fibroadenoma, or other kind of mass. However, the method may be used in any suitable application for imaging a volume of tissue or other suitable object.

Figure 2A:
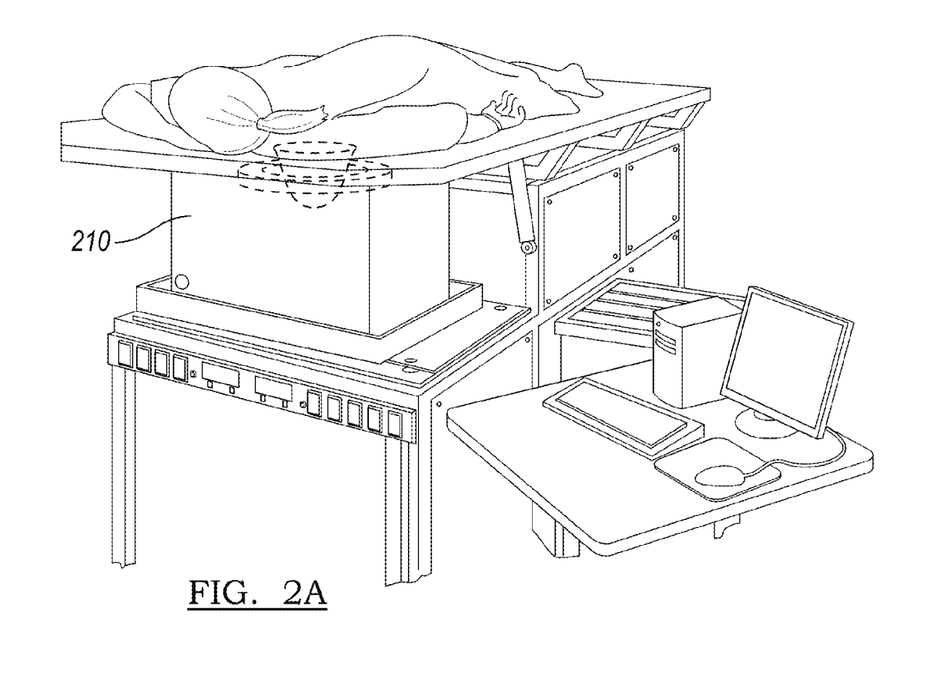
FIGS. 2A-2C are schematics of an exemplary scanner, ring transducer, and rendering images used in and created by the method of a preferred embodiment.
Figure 2B:
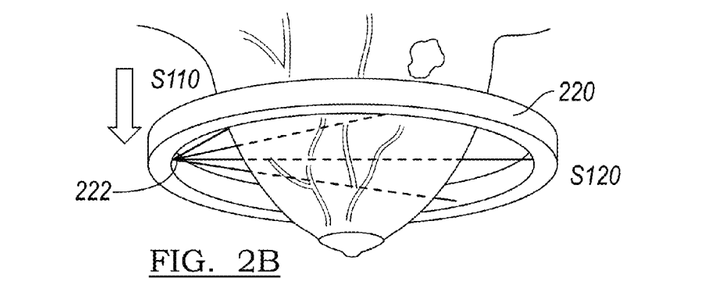
Figure 2C:
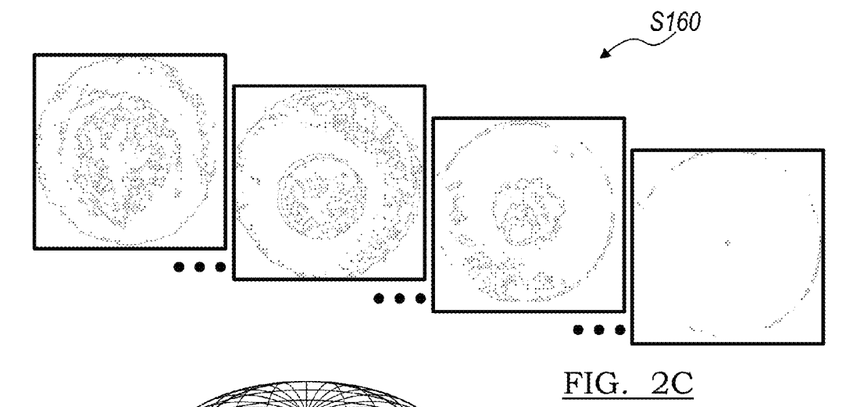

Emitting acoustic waveforms toward the volume of tissue S110 and detecting a plurality of acoustic signals derived from acoustic waveforms S120 interacting with the volume of tissue function to gather acoustic data from which ultrasound images are derived. Emitting acoustic waveforms preferably includes surrounding the volume of tissue with ultrasound transmitters, and more preferably with a ring transducer. The acoustic waveforms are preferably frequencies of approximately 1-10 MHz, or any suitable frequency for medical imaging or other applications. The detected acoustic signals preferably are derived from the interaction between the emitted acoustic waveforms and the tissue, such as scattering including reflection, refraction, diffusion, and transmission of the acoustic waves off and through the tissue. The acoustic signals may travel along a straight, bent, zig-zag, or curved path, or a path of any suitable shape. The steps of emitting acoustic waveforms and detecting a plurality of acoustic signals may be performed with an ultrasound tomographic scanner 200 and methods similar to those described in U.S. Pat. Nos. 6,385,474 and 6,728,567, and U.S. Publication No. 2008/0275344, which are each incorporated in its entirety by this reference. However, any suitable ultrasound device or scanner may be used. As shown in FIG. 2A, the steps of scanning the tissue and detecting acoustic waves are preferably performed during a scan of a patient lying prone on their stomach on a scanner table having a hole opening. The table, which may be made of a durable, flexible material such as sailcloth, preferably contours to the patient's body, thereby increasing scanning access to the axilla regions of the breast and increasing patient comfort. The hole in the table allows the breast (or other appendage) to protrude through the table and be submerged in an imaging tank filled with water or another suitable fluid as an acoustic coupling medium that propagates acoustic waves. As shown in FIG. 2B, a ring-shaped transducer 220 with transducer elements 222 may be located within the imaging tank and encircle or otherwise surround the breast. Multiple emitters that direct safe, non-ionizing ultrasound pulses toward the tissue, and multiple detectors that receive and record acoustic signals scattering from the tissue, are distributed around the ring transducer. During the scan, the ring transducer passes along the tissue, such as in an anterior-posterior direction between the chest wall and the nipple region of the breast to acquire an acoustic data set including measurements such as acoustic reflection, acoustic attenuation, and acoustic speed, preferably at discrete scanning steps, or coronal "slices". The ring transducer may scan step-wise in increments from the chest wall towards the nipple, and/or from the nipple towards the chest wall. However, the ring transducer may additionally and/or alternatively receive data regarding any suitable biomechanical property of the tissue during the scan, and in any suitable direction. The emitting and detecting steps S110 and S120 are preferably quick, such as with a data acquisition time of less than approximately 1 second per "slice", which may help to avoid motion artifacts in the subsequent morphology renderings and enables the use of contrast agents. The emitted and/or detected signals may be beamformed on the transducer. The method may additionally and/or alternatively include retrieving acoustic signals from a storage device such as a hard drive or an online server.

After detecting the plurality of acoustic signals, the method preferably includes performing signal processing of the detected acoustic signals and analyzing the processed signals. For a given transmitter/detector pair of transducers, performing signal processing preferably includes reading and correcting the raw data (detected acoustic signals) for DC variation. An imaginary array is then preferably aliased with an equivalent number of data points as the real data, and Fast Fourier Transform (FFT) transforms the data into the frequency domain, as is known to one ordinarily skilled in the art. A trapezoidal filter is preferably used to bandpass useful frequencies and cut noise, although alternatively any suitable filter (high pass, low pass, etc.) may be used. When transformed into the frequency domain, the FFT of the real signal contains both real and imaginary components over the range of the sampling frequency. Further signal processing may include discarding unusable signal such as "muting" in which recorded signal before the transmission wavefront and/or and after the longest applicable receiving time (e.g. "top muting" or "bottom muting"), further noise reduction processes, and other suitable signal processing steps.

Generally, as known to one of ordinary skill in the art, a generic wave equation may be derived to form a fundamental starting point for analyzing the detected signals. This generic wave equation is given as $$\vec{\nabla}^2 \Phi(\vec{r}, t) - \frac{1}{c^2(\vec{r})} \frac{\partial^2 \Phi(\vec{r}, t)}{\partial t^2} = -q(\vec{r}, t) \quad (1)$$

where $\vec{\nabla}\Phi(\vec{r},t)$ is the gradient of the velocity potential $\Phi$, c is the wave speed propagation, and $q(\vec{r},t)$ is a source function. In one preferred embodiment for the ring transducer geometry, an approximation of the Kirchhoff migration algorithm satisfies Dirichlet boundary conditions (alternatively Neumann, Cauchy, or other suitable boundary conditions) due to direct measurement of the wave amplitude along a ring-shaped or spherical surface S'. Green's Theorem is applied to solve the wave equation (Eq. 1) within the scan region, assuming no internal acoustic sources. The resulting equation, which governs the wave amplitude, is given by the Kirchhoff Integral Theorem $$\Phi(\vec{r}, t) = -\frac{1}{4\pi} \int_0^\infty \oint_{S'} \left( \Phi \frac{\partial \Gamma}{\partial n'} - \Gamma \frac{\partial \Phi}{\partial n'} \right) dA' dt' \quad (2)$$

where Green's function $\Gamma$ is a solution of $$\nabla^2 \Gamma(\vec{r}-\vec{r}', t-t') - \frac{1}{c^2(\vec{r})} \frac{\partial^2 \Gamma(\vec{r}-\vec{r}', t-t')}{\partial t^2} = -\delta(\vec{r}-\vec{r}')\delta(t-t') \quad (3)$$

within the integrating volume. In three dimensions, the free-space Green's function that satisfies Eq. 3 within a region of unvarying sound speed is given by $$\Gamma = \frac{\delta(t \pm |\vec{r}-\vec{r}'|/c - t')}{|\vec{r}-\vec{r}'|} + G(\vec{r}, t | \vec{r}', t') \quad (4)$$

where G satisfies the homogeneous differential equation $$\vec{\nabla}^2 G(\vec{r}, t) - \frac{1}{c^2(\vec{r})} \frac{\partial^2 G(\vec{r}, t)}{\partial t^2} = 0 \quad (5)$$

Assuming the real wave amplitude is obtained from the detected acoustic signals as measurement of the wave amplitude along a "spherical" surface S', $\delta\Phi/\delta n'$ remains to be calculated from the measured real wave amplitude, as defined by the Dirichlet boundary conditions (alternatively Neumann, Cauchy, or other suitable boundary conditions). A preferred Green's function vanishes on the surface S' to eliminate the last term of Eq. 2, represented by $\tilde{\Phi}$ in $$\Phi(\vec{r}, t) = -\frac{1}{4\pi} \int_0^\infty \oint_{S'} \Phi \frac{\partial \Gamma}{\partial n'} dA' dt' + \frac{1}{4\pi} \int_0^\infty \oint_{S'} \Gamma \frac{\partial \Phi}{\partial n'} dA' dt' \quad (6)$$

$$\Phi(\vec{r}, t) = \hat{\Phi}(\vec{r}, t) + \tilde{\Phi}(\vec{r}, t).$$

The conventional image method for planar imaging, as understood by one of ordinary skill in the art, cannot be applied to exactly satisfy the boundary conditions given here for a ring or sphere of radius a, but the obliquity factor from the results of the image method on a planar surface can be adapted to the ring array by geometric interpretation and is valid as long as the wavelength of the acoustic signal is much smaller than the radius of curvature of the aperture (arrangement of the detecting transducers). Neglecting the contribution of the $\tilde{\Phi}$ term to the reconstruction and proceeding with calculations using the free-space Green's function (Eq. 4) where $|\vec{r} - \vec{r}'| = \sqrt{r^2 + r'^2 - 2rr'\cos\gamma}$, $r = |\vec{r}|$, $r' = |\vec{r}'|$ in polar coordinates and $\gamma$ is the angle between position $|\vec{r}|$ and the Green's function source position $|\vec{r}'|$. Substituting Green's function (Eq. 4) with G=0 into the first term of the Kirchhoff Integral Theorem (Eq. 2) yields $$\hat{\Phi}(\vec{r}, t) = \frac{1}{8\pi} \int_0^{2\pi} \int_0^{\pi'} \frac{a(a^2 + R^2 - r^2)}{R^3} \left[\Phi - t_R \frac{\partial \Phi}{\partial t'}\right]_{t' = t + t_R} d\Omega', \quad (7)$$

$$\hat{\Phi}(\vec{r}, t) = \frac{1}{4\pi} \int_0^{2\pi} \int_0^{\pi} \frac{a^2 \cos\theta}{R^2} \left[\Phi - t_R \frac{\partial \Phi}{\partial t'}\right]_{t' = t + t_R} d\Omega',$$

where $R = (r^2 + a^2 - 2ar\cos\gamma)^{1/2}$ is equal to $|\vec{r} - \vec{r}'|$ evaluated with r'=a, and $\hat{\Phi}$ indicates evaluation of only the first term in the integrand.

Figure 3:
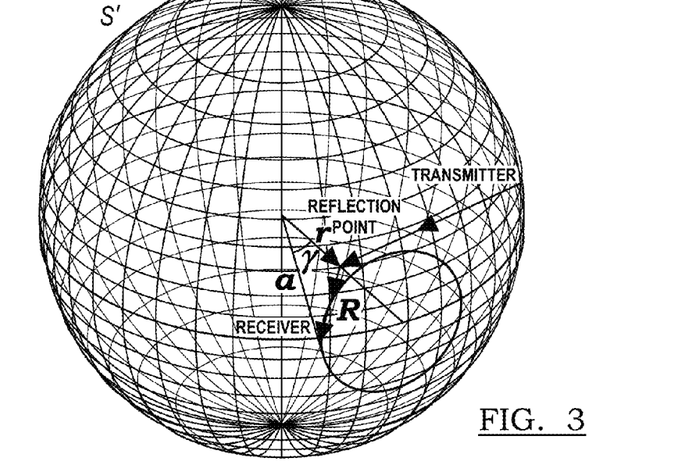
FIG. 3 is a schematic of spherical geometry in derivation of the reconstruction algorithm used in the method of a preferred embodiment.

The integral of Eq. 7 is preferably converted into a calculable discrete form for a finite number of transducers along a circular array (but may alternatively be modified for any suitable geometry). In one variation, the conversion assumed spherical spreading from the reflection point as described by Huygens' Principle, such that the intersection of the reflected spherical wavefront and the spherical sampling surface (FIG. 3) creates a circle. This circle, for a single receiver, is evaluated as a semi-annular weighted section and produces the migration formula $$\Phi(\vec{r}, t) = \sum_{\substack{receiver \\ positions}} \frac{\sin\left(\frac{\Delta\gamma}{2}\right)}{2} \frac{a(a^2 + R^2 - r^2)\sin\gamma}{R^3} \left[\Phi - t_R \frac{\partial \Phi}{\partial t'}\right]_{t' = t + t_R} \quad (8)$$

where $\Delta\gamma$ is equal to $\pi$ divided by the number of transducers. In another variation, considering the contributions from the measured positions on the ring transducer, the term $\sin\gamma$ is replaced by a constant and all out of plane information is aliased to zero. The migration formula of Eq. 8 is preferably used to map the amplitude of the wave at any point and time within the sample surface area.

Generating a plurality of variable attenuation maps S130 functions to generate an array of attenuation coefficients for regions of the volume of tissue, which represents the degree to which an acoustic signal is attenuated (decreases in amplitude) when passing through the tissue. The attenuation coefficient for a fluid can be expressed $$\alpha = \frac{\omega^2}{2\rho_o c^3} \left[\frac{4\eta}{3} + \zeta + K_{th}\left(\frac{1}{c_V} - \frac{1}{c_p}\right)\right]. \quad (9)$$

where $\omega$ is the frequency of the signal, c is the speed of the wavefront of the signal, $K_{th}$ is the thermal conductivity of the fluid, $\rho$ is the density of the fluid, $\eta$ is shear viscosity of the fluid, $\zeta$ is bulk viscosity of the fluid, and $c_v$ and $c_p$ are the specific heat per unit mass at a constant volume and pressure, respectively. The amplitude A of a wave then decays from an initial amplitude $A_o$ following the equation $$A = A_o \cdot e^{-\alpha \cdot d} \quad (10)$$

at a depth d from the initial amplitude. Here, the units of the attenuation coefficient $\alpha$ are nepers per unit length. As one of ordinary skill in the art will know, in common practice for sound waves, the unit to express amplitude is the decibel (dB), which is also an exponential ratio with base 10 instead of e. The effect of signal attenuation in conjunction with geometrical spreading (in two-dimensional and three-dimensional space) can rapidly decay the amount of energy detectable in the acoustic signal. For materials of diagnostic ultrasound, the attenuation coefficients are approximated by a linear frequency dependence.

Generating a plurality of variable attenuation maps S130 preferably includes generating at least one attenuation image of the scan region. Each of the plurality of attenuation images is preferably a two-dimensional slice of the scan region (e.g. coronal slice of the volume of tissue) that represents an array of attenuation coefficients. In other embodiments, the attenuation image may be a three-dimensional attenuation model of the scan region (such as a model formed in a three-dimensional manner or combined from a stack of two-dimensional images). The attenuation image preferably includes multiple grid elements (e.g. pixels) such that each grid element represents a corresponding attenuation coefficient for a respective region of the scan region, including the volume of tissue and the acoustic coupling medium (such as the fluid of the tank in which the tissue is submerged). In particular, each attenuation image may be created using a measure of attenuation of transmission signals and assuming a broad frequency band signal (or any suitable frequency band signal). Alternatively, each attenuation image may be created on a frequency-dependent and/or transducer-dependent basis to account for frequency and directional dependence of absorption and scatter on the signal.

Generating a plurality of variable attenuation maps S130 preferably further includes generating at least one path integral attenuation map S132 or path average attenuation map as an approximation of the path integral attenuation map. Each path integral or path average attenuation map corresponds to a particular transducer that detects signals, and each reflection point on the path average attenuation map represents the average attenuation of a signal traveling from the transmitter, to the reflection point, and back to the receiver or detecting transducer. For each detecting transducer (or at least a portion of the transducers) and each signal path of the detecting transducer, generating a path average attenuation map preferably includes approximating the integral $$\int_o^d \alpha \cdot dl \tag{11}$$

where α is the attenuation coefficient and the integral is taken over the signal path from the transmitter to the reflection point and to the receiver. In a preferred embodiment, the integral of Eq. 11 is approximated by averaging the attenuation coefficients α of grid elements along an acoustic signal path, multiplying the averaged attenuation coefficient by the approximate length of the acoustic signal path (e.g. round-trip path from and to the origin and end point of a reflected acoustic signal), and repeating the averaging and multiplying steps for each acoustic signal path for the particular transducer. The signal path length may be approximated by assuming a fixed distance for each pixel and multiplying the fixed distance by the number of pixels in the path, or by any suitable method. For instance, in an exemplary process to generate a path average attenuation map for a particular transducer, each of multiple particular coordinate locations in the scan region is selected and the value of path average attenuation to that point is calculated and stored for that particular transducer, such that the aggregated path average attenuations form a path average attenuation for that particular transducer. The process may be repeated for a portion or all of the transducers. In alternative embodiments, generating a path average attenuation map may include any other suitable step that approximates and/or accurately calculates the integral.

Modifying at least a portion of the detected acoustic signals S150 based on one or more variable attenuation maps functions to modify attenuated acoustic signals. Modifying at least a portion of the detected acoustic signals preferably includes amplifying at least a portion of the detected acoustic signals for a detecting transducer based on the path average attenuation map for the detecting transducer. The amplification preferably includes multiplying the detected acoustic signals by a gain or factor including a path average attenuation corresponding to the detected acoustic signal. In a preferred embodiment, the gain factor includes an exponent of the corresponding path integral attenuation as calculated in generation of the path attenuation map for the detecting transducer. For instance, the modified signal $A_o$ may be expressed in terms of the detected signal $A_f$ and the path integral attenuation for the detected signal path as $$A_o = A_f \cdot 10^{\frac{1}{20} \int_0^d \alpha \cdot dl} \tag{12}$$

where the attenuation coefficient α is expressed in dB/cm. However, modifying detected acoustic signals based on one or more variable attenuation maps and/or path average attenuation maps may include amplifying or boosting the detected attenuated acoustic signal in any suitable manner.

Generating a reflection rendering of the volume of tissue S160 based on the modified acoustic signals functions to create a representative characterization of the volume of tissue based on reflected acoustic signals. Although some ray-based models and other wave-based models may be used to generate a reflection rendering, in a preferred embodiment the method includes utilizing a migration algorithm, in particular the Kirchhoff migration algorithm. The Kirchhoff migration algorithm, as described above, is preferably modified for a ring transducer geometry, but may alternatively be modified for any suitable transducer geometry. However, any alternative migration formula or other suitable algorithm may additionally and/or alternatively be used to incorporate the modified acoustic signals (amplified based on the variable attenuation maps) into the reflection renderings.

Figure 4A:
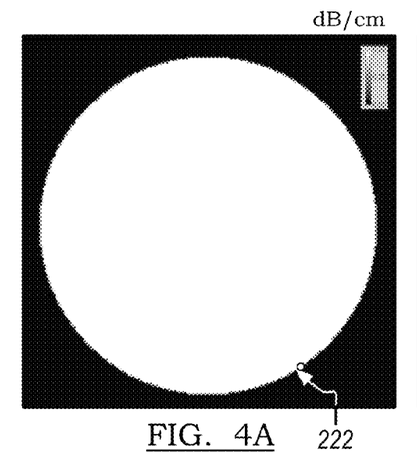
FIGS. 4A-4D are example images of the constant attenuation map, variable attenuation map, path average attenuation map, and the difference between the constant and variable attenuation maps, created by the method of a preferred embodiment.
Figure 4B:
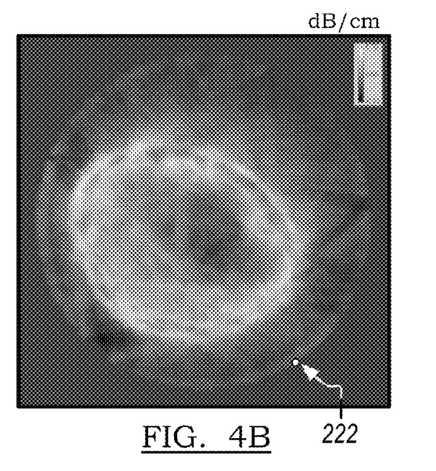
Figure 4C:
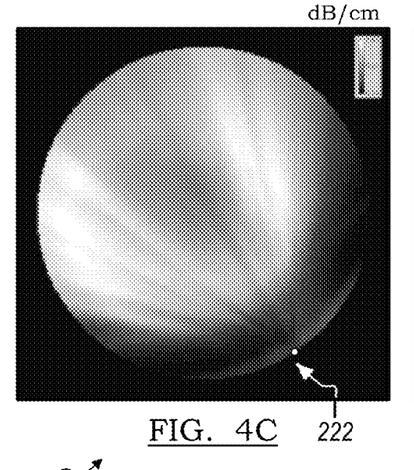
Figure 4D:
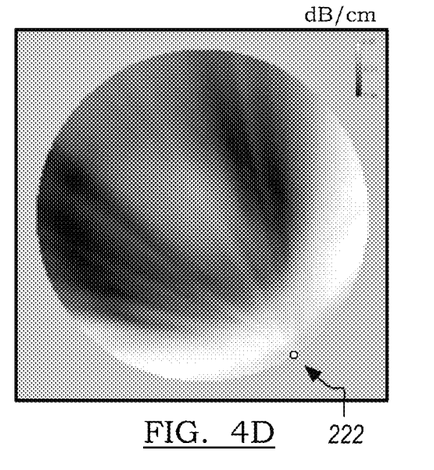

Imaging with the use of a variable attenuation coefficient may result in significantly different and more accurate characterization of the tissue and the rest of the scan region than imaging with the use of a constant attenuation coefficient. As shown in FIG. 4A, use of a constant attenuation coefficient may oversimplify the attenuation characteristics of the scan region, such as inaccurately characterizing the entire scan region with the volume of tissue and the acoustic coupling medium as having a homogenous and uniform attenuation coefficient. As shown in FIGS. 4B and 4C respectively, the variable attenuation map and path average attenuation map of the scan region highlight the different attenuation characteristics between the tissue and the acoustic coupling medium, as well as between different regions of the volume of tissue itself. As shown in FIG. 4D, the difference between the constant and variable attenuation maps illustrates that the constant attenuation model overestimates the attenuation of the acoustic coupling medium (water) and largely underestimates the attenuation of the volume of tissue. Amplification with the variable attenuation maps properly compensates for attenuated signals by properly boosting signals without creating hypoechoic and hyperechoic shadows in the resulting ultrasound images, and without creating unnecessary noise in the water.

Generating a reflection rendering S160 preferably involves considering each point in the scan region as a point reflector and reconstructing the amplitude of an acoustic waveform when the waveform intersects each particular point, as a measure of reflectivity of each point within the scan region. Reconstruction of the amplitude of waveforms is preferably limited to those waveforms reflecting within an approximated maximum total internal reflection angle of the waveform, which may be calculated as an expected maximum difference of internal waveform sound speeds of the waveform across boundaries. In a preferred embodiment, reconstruction of the amplitude of the waveforms is limited to a portion of the receiving transducers known as the aperture. In one example, generating a reflection rendering uses each emitting transducer as the center receiving element and an equal number of nearest-neighbor transducers on each side of the emitting transducer to reconstruct the image. This aperture can be modified (i.e. number of receiving transducers whose received signals are used) to optimize or otherwise alter parameters such as computational speed or image quality. Furthermore, the reconstruction algorithm may include a point model (e.g. treating each pixel with a predetermined size and as a point in space) or a bin model that is known by one ordinarily skilled in the art.

In one variation, the amplified signal may additionally and/or alternatively be filtered with a Hilbert transform in the frequency domain to create an analytic signal. Creating the analytic signal in the frequency domain preferably includes doubling the positive values of the real and imaginary frequencies of the signal, aliasing to zero the negative values of the real and imaginary frequencies, and inverse-transforming the signal into the time domain. The magnitude of the inverse-transformed signal (which includes both real and imaginary components) is the envelope of the original amplified signal and may be used in generating a reflection rendering of the volume of tissue.

Figure 5:
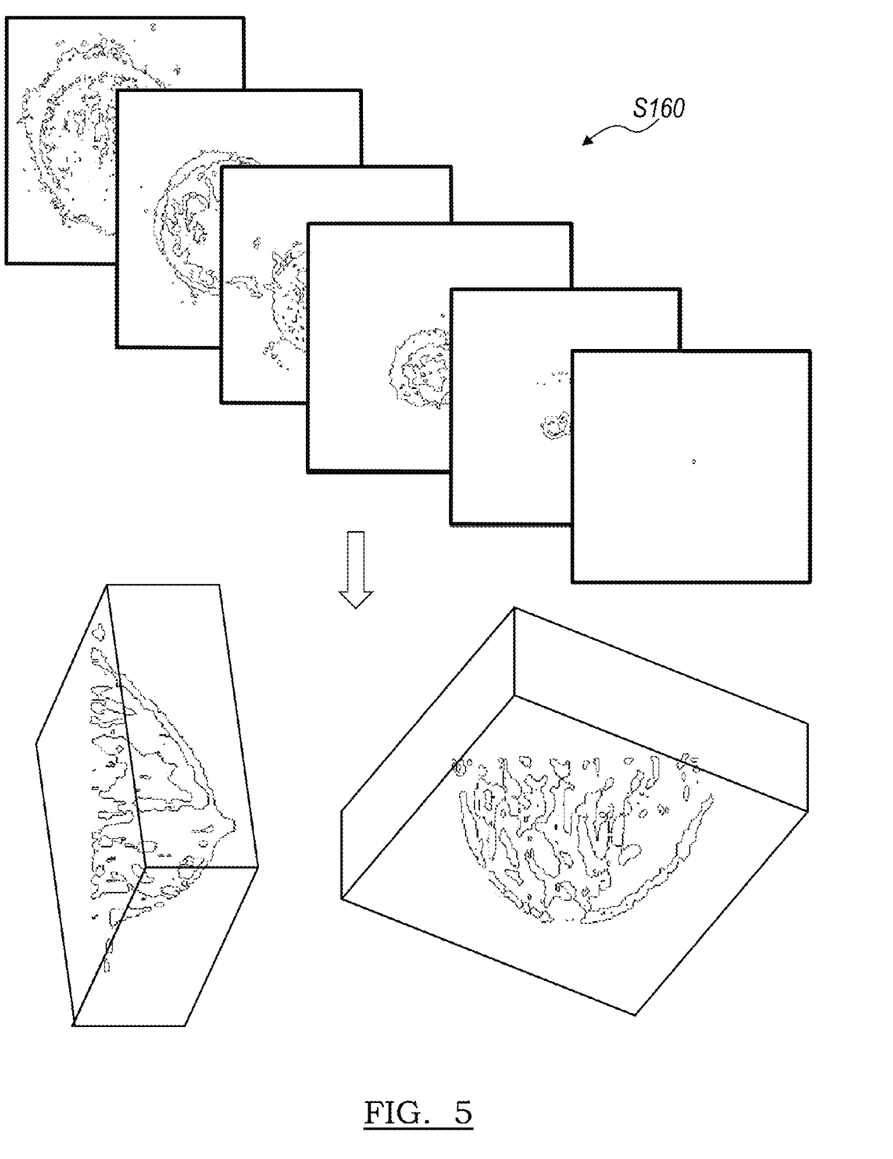
FIG. 5 is a schematic of generating a reflection rendering in the method of a preferred embodiment.

As shown in FIG. 5, generating a reflection rendering S160 preferably includes generating one or more 2D reflection renderings, and/or one or more 3D reflection renderings (e.g. by scanning in a 3D manner, or combining multiple 2D reflection renderings). Furthermore, a 3D reflection rendering may be resliced to allow projection of 3D volume information into other suitable planes, such as transverse and sagittal planes. The reflection rendering may be further manipulated for adjustments in brightness, contrast, sharpness, noise, and/or other parameters such as with a smoothing algorithm or other image treatment processes. The reflection rendering may utilize raw radiofrequency (RF) source data, and/or be converted into an amplitude B-mode ultrasound image, flash B-mode ultrasound image, or any other suitable image.

In some variations, the method 100 may further include generating a sound speed rendering or map S140 of the volume of tissue and/or scan region and generating a plurality of signal variable travel time maps S142 from the sound speed rendering. The sound speed renderings and attenuation maps may be used in combination to provide improved quality of the reflection rendering images. The sound speed rendering(s) and/or time travel maps may be used to further improve the variable attenuation map(s) and/or path average attenuation maps to improve the resulting reflection rendering images. In one variation, the step of generating a plurality of path integral attenuation maps includes, for each detecting transducer, tracing a plurality of acoustic signal paths at least partially based on the sound speed rendering and integrating attenuation along each of the traced acoustic signal paths. The acoustic signal paths (which may be straight, bent, curved, or have other non-straight shapes due to scattering such as refraction) may be traced based on wave refraction as calculated, shown, or otherwise derived from the sound speed rendering. Attenuation along the traced acoustic signal paths may be integrated to form a signal path integral attenuation map that is used in the reflection rendering generation process as described above.

Figure 6A:
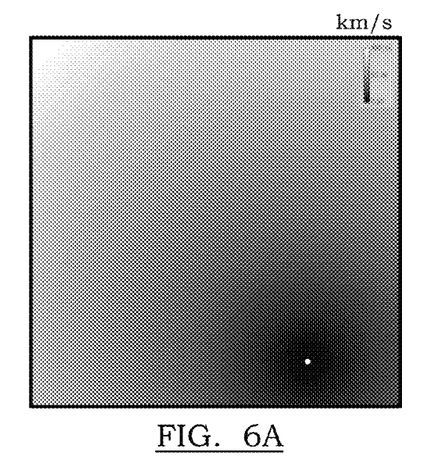
FIGS. 6A-6D are example images of the constant sound speed map, variable sound speed map, variable travel time map, and difference between a constant and variable sound speed map, created by the method of a preferred embodiment.
Figure 6B:
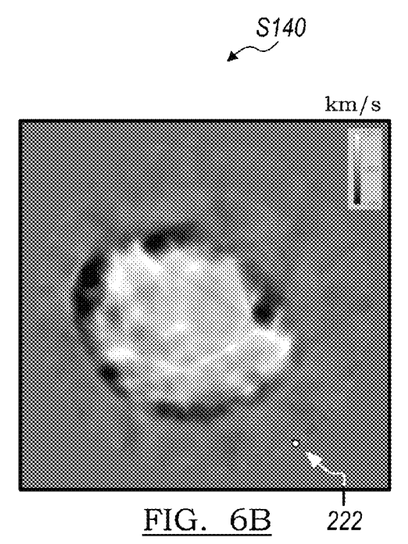
Figure 6C:
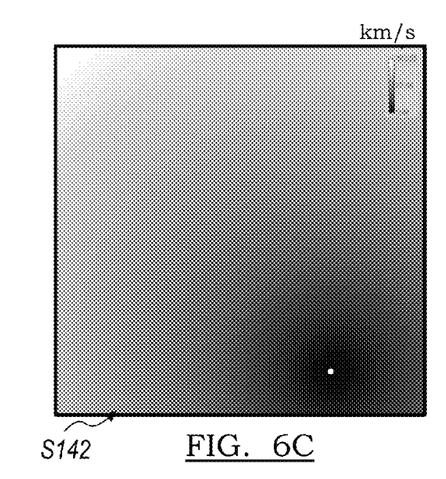
Figure 6D:
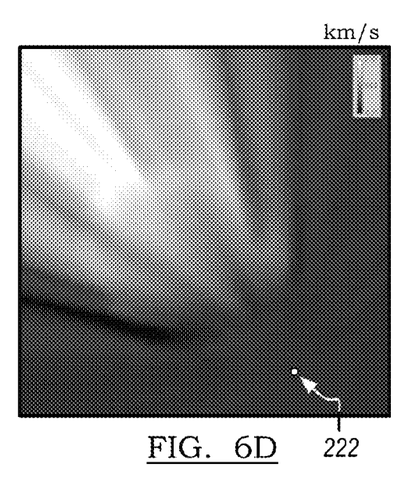

Similar to the reflection and attenuation renderings, the sound speed rendering may be a set of 2D images, or a 3D image (e.g. combined from a set of 2D images or scanned in a 3D manner). Each signal variable travel time map preferably corresponds to a respective transmitting transducer and represents travel time for each detected signal for the respective transmitting transducer. Sound speed varies when propagating through different types of mediums, including different kinds of tissue and acoustic coupling medium. For instance, water has a sound speed of approximately 1.480 km/s, while fatty tissue and muscle have sound speeds of approximately 1.450 km/s and 1.585 km/s, respectively. In some applications, assuming a constant sound speed model (such as that reflected in a signal travel time map shown in FIG. 6A) within a scan region that contains different materials results in more inaccurate and lower quality imaging. Generating a sound speed rendering is preferably based on transmitted acoustic signals and results in a sound speed map (FIG. 6B) for each of at least a portion of the detecting transducers, such that the sound speed map represents variable sound speeds across the scan region. In a preferred embodiment, an eikonal solver converts each sound speed map into a slowness map, which the eikonal solver steps through to create a travel time table respective to the position of the corresponding transmitting transducer. The resulting travel time table (FIG. 6C) generated from a variable sound speed model represents travel time of acoustic signals from the transmitting transducer to points throughout the scan region. Generating an attenuation map and/or generating a reflection rendering may incorporate the travel time map. For instance, signal time-of-flights from the travel time table may used to determine accurate values for t and $t_R$ for summation in Eq. 8, which results in more accurate images and higher image quality. Furthermore, the variable sound speed map and signal travel time tables allow better alignment of wave amplitude interference (both constructive and destructive). As shown in FIG. 6D, the difference between values in a variable travel time table and a constant travel time table (representing the difference between variable and constant sound speed models) is relatively small in the water or acoustic coupling region, but the difference grows rapidly in the region of and beyond the heterogeneous volume of tissue. For example, in a comparison of renderings of the volume of tissue produced with a constant sound speed model and with a variable sound speed model, the image of the tissue using the variable sound speed model benefits from enhanced contrast and sharper edges as shown by the skin, internal fibrous structure, and cyst wall. Furthermore, acoustic signal that was otherwise lost with use of a constant sound speed model is retained and amplified by constructive interference between wave amplitudes as a result of the variable sound speed model. In other words, imaging with the use of a variable sound speed model may result in significantly different and more accurate characterization of the tissue and the rest of the scan region than imaging with the use of a constant sound speed model.

Figure 7A:
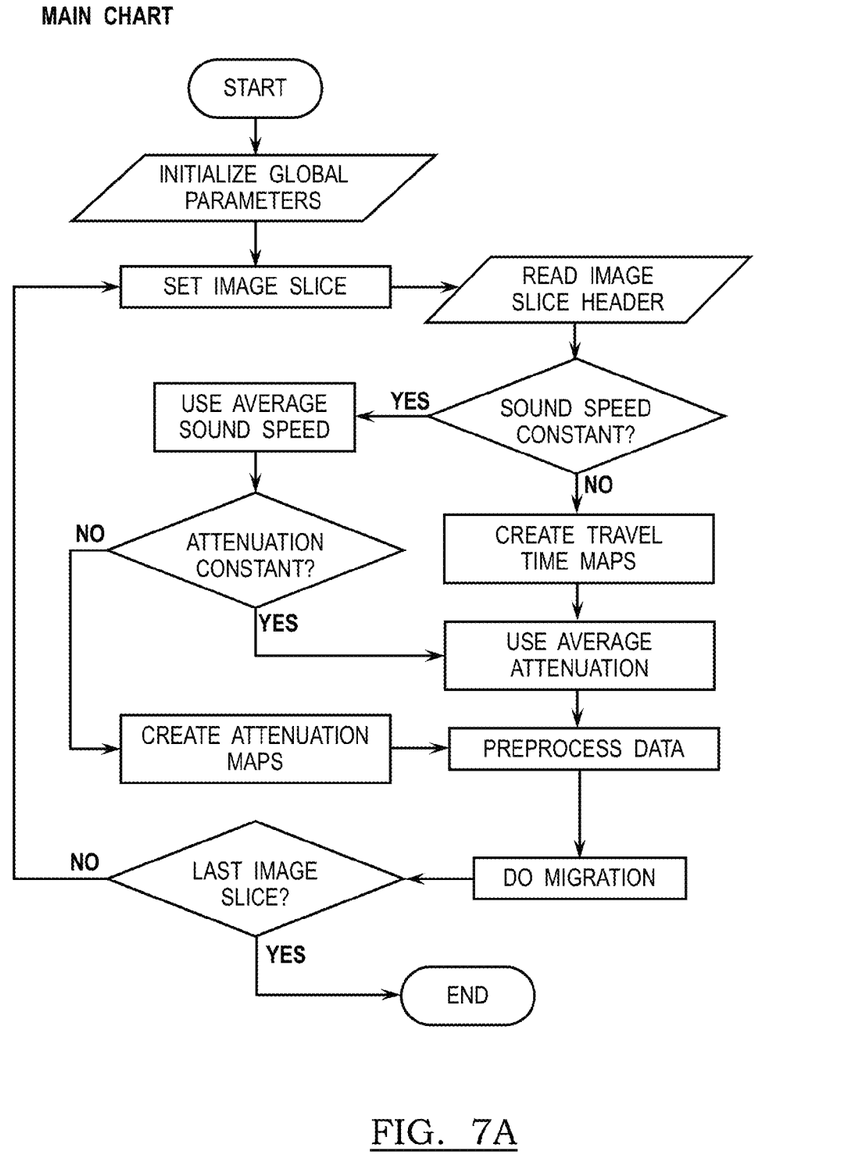
FIGS. 7A-7E are example flowcharts of the method of a preferred embodiment.

In one preferred embodiment, as shown in the schematic of FIG. 7A, the method of imaging a volume of tissue includes scanning the tissue (transmitting ultrasound waves and receiving scattered waves after the ultrasound waves interact with the tissue) slice by slice in a repetitive process for each slice. For each repetition, a slice is identified and characterized by a slice header which includes initial information such as whether sound speed and attenuation coefficients are to be treated as constant. If the sound speed is to be characterized with a variable sound speed model, then a set of travel time maps for the slice is generated such as in the process as described above, or any suitable process. Alternatively, if the sound speed is to be characterized with a constant sound speed model, then an assumed constant sound speed (e.g. predetermined average sound speed for the tissue or the entire scan region) is to be utilized. Similarly, if the signal attenuation is to be characterized with a variable attenuation model, then a set of attenuation maps and/or path integral or average attenuation maps are generated such as in the process described above, or any suitable process. Alternatively, if the signal attenuation is to be characterized with a constant attenuation model, then an assumed constant attenuation coefficient (e.g. predetermined average attenuation coefficient for the tissue or entire scan region) is to be utilized. With the desired sound speed and attenuation models selected, the acoustic data for the slice undergoes preprocessing and image migration is performed for the slice. This process is repeated for all of the desired slices of the scan region. For a particular scan, all slices are preferably characterized with a variable sound speed model and variable attenuation model, but some or all of the slices may alternatively be characterized with a constant sound speed model and/or variable attenuation model in any combination.

Figure 7B:
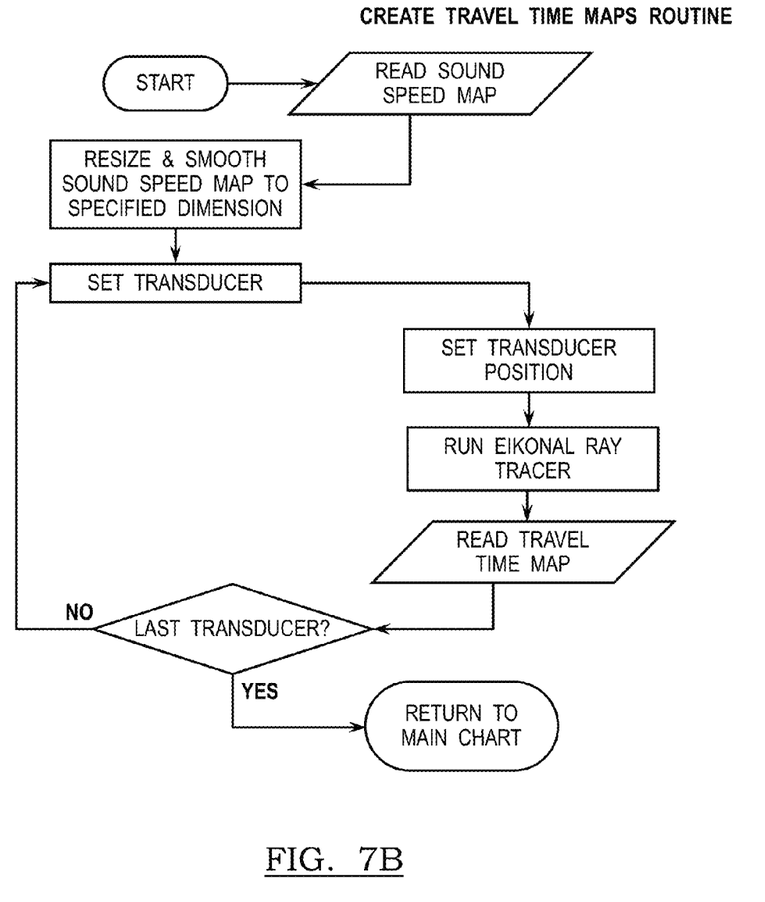

As shown in the schematic of FIG. 7B, in an exemplary process to generate a set of signal travel time maps for a particular slice, a sound speed map for the slice is generated and/or retrieved. The sound speed map may be processed such as by resizing and/or smoothing to a specified dimension. For a particular transducer and its transducer position, an eikonal ray tracer solver takes an input of the sound speed map and generates a signal travel time map. The signal travel time map generating process may be further repeated for a portion or all of the transducers for the slice.

Figure 7C:
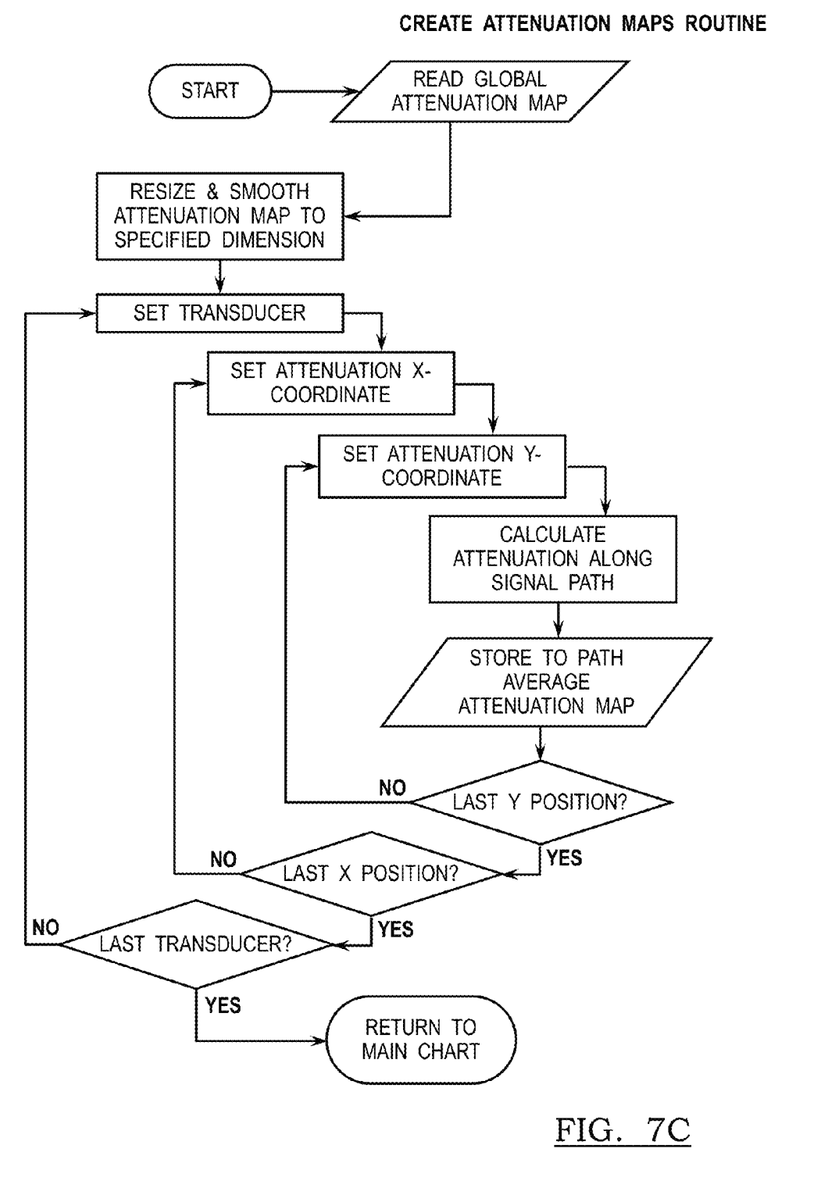

As shown in the schematic of FIG. 7C, in an exemplary process to generate a path average attenuation map for a particular image slice, a global attenuation map or image is generated and/or retrieved. The global attenuation map may be processed such as by resizing and/or smoothing to a specified dimension. For a particular transducer, a particular location in the scan region is selected with an x-coordinate and a y-coordinate, and a value of path average attenuation to that location is calculated (e.g. by averaging the discrete grid-element attenuation coefficients along the path and multiplying by the path length) and stored to that particular location in a path average attenuation map for that particular transducer. In this example, the calculation and storing of the path average attenuation is repeated for multiple x- and y-coordinate locations for that particular transducer. Alternatively, the path average attenuations may be sequentially calculated in a stepwise manner according to polar coordinates, cylindrical coordinates, or in any other suitable order. The path average attenuation map generating process may be further repeated for a portion or all of the transducers for the slice. However, in an alternative variation the method may include generating a set of path integral attenuation maps, such as by tracing acoustic signal paths on sound speed maps and integrating attenuation along each acoustic signal paths.

Figure 7D:
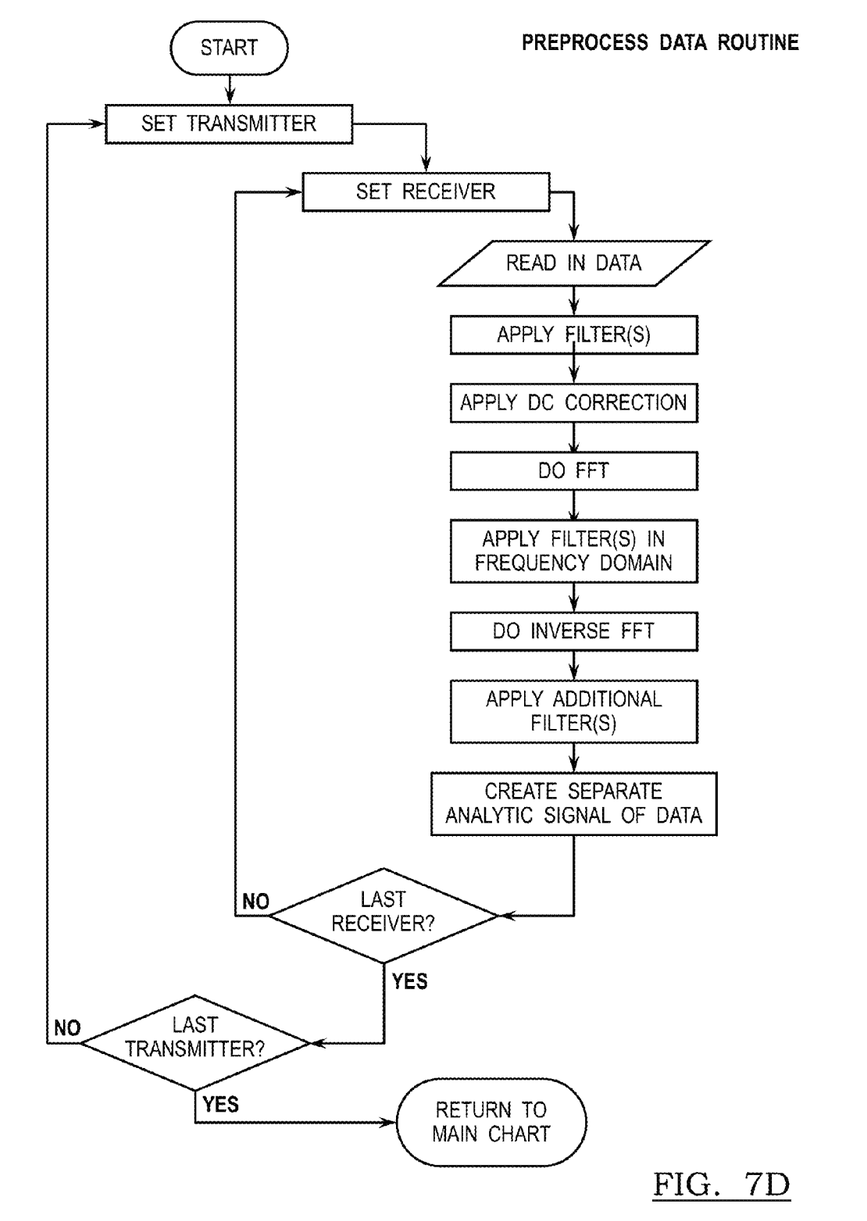

As shown in the schematic of FIG. 7D, the preprocessing step for a particular image slice may be performed by a processor that steps through signals of each receiving transducer of each transmitting transducer. The acoustic signal of each receiving transducer is filtered and undergoes DC correction, is converted by a Fast Fourier Transform (FFT) to the frequency domain, filtered in the frequency domain, converted by an inverse FFT to the time domain, and/or modified by other suitable filters. The processor may further create a separate analytic signal of the acoustic data. The preprocessing step may be further repeated for a portion or all of the transducers for the slice.

Figure 7E:
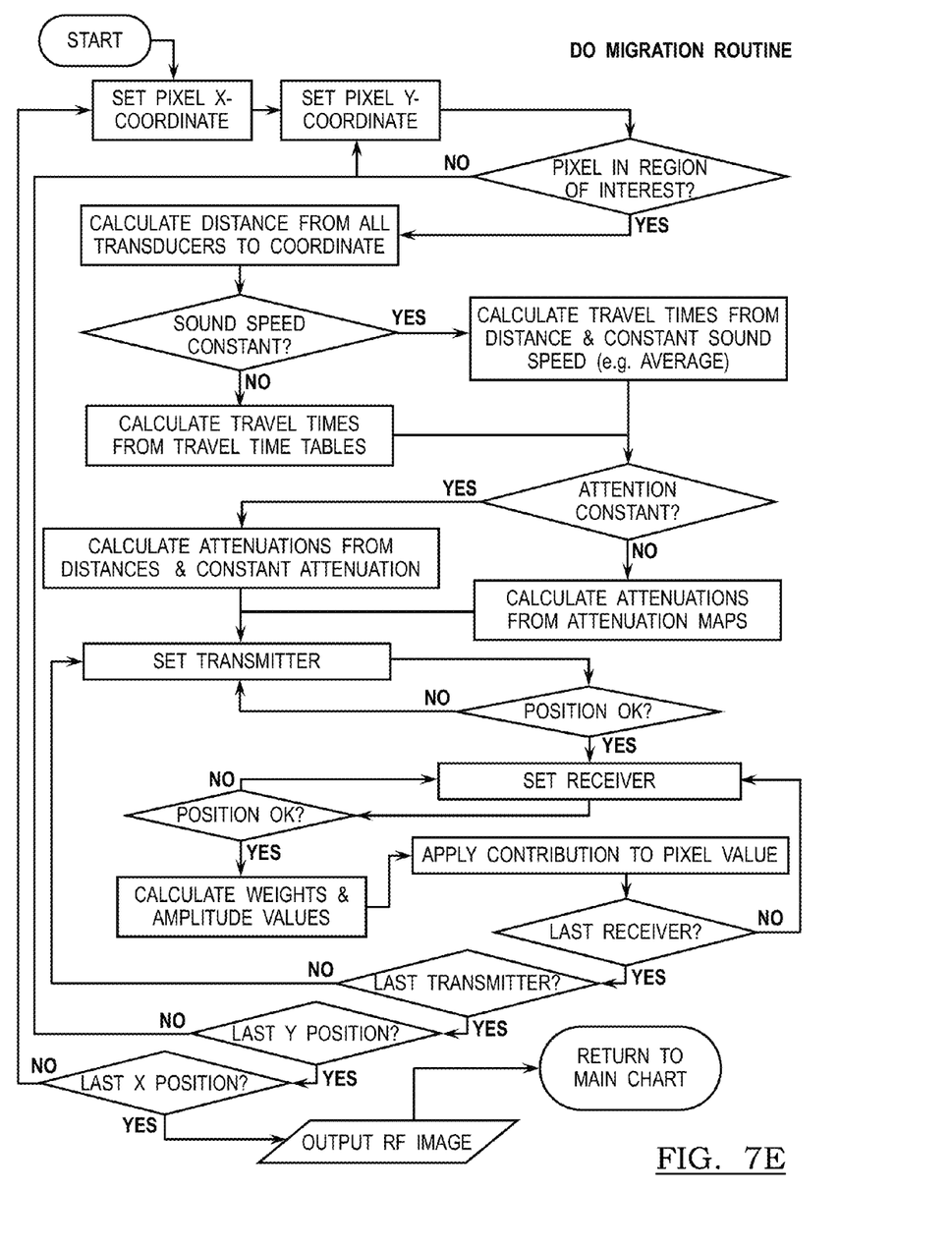

As shown in the schematic of FIG. 7E the image migration step for a particular image slice may be performed by a processor that steps through particular locations of the scan region and calculates signal travel time and attenuation information for that location from travel time tables (which may depend on whether the location is to be characterized as having constant or variable sound speed), attenuation maps and/or path average attenuation maps (which may depend on whether the location is to be characterized as having constant or variable attenuation). The processor may, for each receiving transducer of each transmitting transducer, use the signal travel time and attenuation information to generate image data for that location of the image slice. The migration step may be further repeated for some or all locations of the image slice. The processor preferably aggregates the image data to create an RF image of the slice, which may be further transformed into a B-scan ultrasound image, and/or undergo smoothing or other modifications.

In other variations of this method, the systematic repetitions of calculations (e.g. for each location in the scan region, each emitting transducer, or each detecting transducer) may be nested in any suitable combination and/or permutation.

EXAMPLE

In one specific example of an, embodiment of the invention, the Kirchhoff image migration reconstruction algorithm was modified for an ultrasound transducer having transducer elements distributed around a ring geometry. The ring transducer contained 256 individual acoustic elements evenly circumferentially distributed around the inner surface of the ring. A patient was positioned on a table with an opening and submerged her breast through the opening into an imaging tank that contained the transducer ring and filled with water as an acoustic coupling medium between the ring transducer and breast tissue. The scan of the breast tissue was initialized with the transducer positioned near the chest wall of the patient. At this initial position, a first transducer element fired its ultrasonic pulse with all receiving transducers detecting and recording the resulting acoustic signals, and this step was repeated with the rest of the transducer elements firing in sequence. After all transducer elements fired their respective ultrasonic pulses, the ring transducer then translated stepwise along the coronal axis, repeating the firing sequence at each step to generate acoustic data for each "slice" until the desired length of the breast was scanned. Allowing for an additional interval to allow for the vibrational settling of the water between firing, data for each slice took approximately a second to acquire. Each acoustic element was configured to emit a primary ultrasonic pulse wave at broadband frequencies centered around 2 MHz, and to detect pulses for a period of approximately 0.175 ms after firing, with a sampling rate between approximately 6.25 MHz and 8.33 MHz.

Figure 8A:
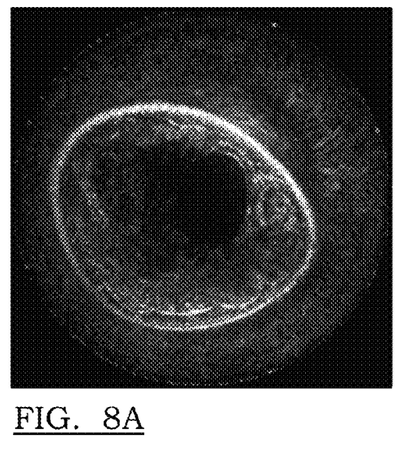
FIGS. 8A-8C are images from an example scan, generated by reconstruction with a constant attenuation model, variable attenuation model, and variable sound speed and attenuation models, respectively, including those created by the method of a preferred embodiment.
Figure 8B:
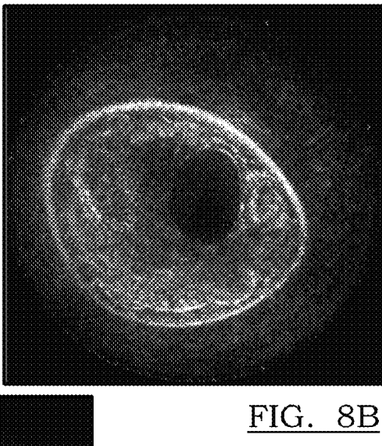
Figure 8C:
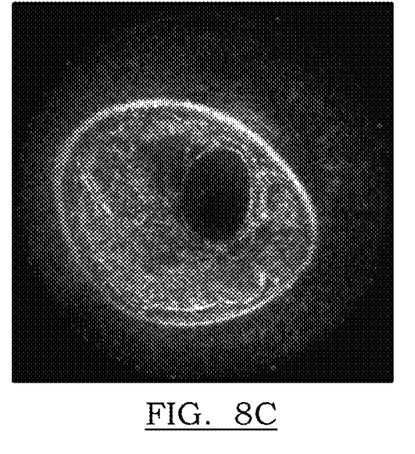

The acquired acoustic data was read from the raw signal file and analyzed by a processor to generate two sets of images: one set of images using a constant attenuation model with an attenuation coefficient of 0.5 dB/cm, and a second set of images using a variable attenuation model as described above. Compared to the images generated with a constant attenuation model (FIG. 8A), the images generated with appropriate variable attenuation maps and path average attenuation maps (FIG. 8B) provide for a clearer and more accurate reflection rendering of the breast tissue, such as properly boosting signals attenuated by tissue without overestimating or underestimating signal attenuation in particular regions, nor creating unnecessary noise in the water. The processor further generated a third set of images using both a variable sound speed model and a variable attenuation model. As shown in FIG. 8C, in the images generated using both variable sound speed and variable attenuation models, the cyst wall and skin are more complete and in focus compared to the images generated using constant sound speed and constant attenuation models shown in FIG. 8A.

As a person skilled in the art of medical imaging will recognize from the previous detailed description and from the figures and claims, modifications and changes can be made to the preferred embodiments of the invention without departing from the scope of this invention defined in the following claims.

We claim:

1. A method for imaging a volume of tissue within an acoustic coupling medium in a scan region, comprising:
   emitting acoustic waveforms from transmitting transducers toward the volume of tissue;
   detecting, with detecting transducers, a plurality of acoustic signals derived from acoustic waveforms interacting with the volume of tissue;
   generating, from the plurality of acoustic signals, a plurality of variable attenuation maps, wherein each variable attenuation map corresponds to a respective detecting transducer and the acoustic signals detected by the respective detecting transducer, and wherein each variable attenuation map includes a plurality of variable attenuation coefficients mapped to the scan region, comprising the volume of tissue and the acoustic coupling medium, for the corresponding detecting transducer, wherein at least a subset of the plurality of variable attenuation coefficients, characterizing the acoustic coupling medium, comprises unequal variable attenuation coefficients, such that the subset is not defined by a constant attenuation coefficient;

transforming at least a portion of the plurality of acoustic signals into a set of modified acoustic signals based upon at least one variable attenuation map of the plurality of variable attenuation maps; and generating a reflection rendering of the volume of tissue based upon the set of modified acoustic signals.

2. The method of claim 1, wherein emitting acoustic waveforms towards the volume of tissue includes surrounding the volume of tissue with ultrasound transducers.

3. The method of claim 2, wherein surrounding the volume of tissue includes encircling a human breast with a ring transducer.

4. The method of claim 1, wherein generating a plurality of variable attenuation maps includes generating an image of the scan region with discrete grid elements, wherein each grid element represents a corresponding attenuation coefficient.

5. The method of claim 4, wherein generating a plurality of variable attenuation maps includes generating a set of two-dimensional images of attenuation coefficients of the scan region, each two-dimensional image corresponding to a cross-section of the scan region.

6. The method of claim 4, wherein generating a plurality of variable attenuation maps further includes generating a plurality of path integral attenuation maps, wherein each path integral attenuation map corresponds to a detecting transducer and represents path integral attenuation for each of a plurality of acoustic signal paths to the detecting transducer.

7. The method of claim 6, wherein generating a plurality of path integral attenuation maps includes, for each detecting transducer:

averaging the attenuation coefficients of grid elements along an acoustic signal path;

multiplying the averaged attenuation coefficient by a length of the acoustic signal path characterized by a round-trip path bounded by an origin and an end point of a reflected acoustic signal; and repeating the averaging and multiplying steps for each of the plurality of acoustic signal paths.

8. The method of claim 6, wherein generating a plurality of path integral attenuation maps includes, for each detecting transducer:

tracing a plurality of acoustic signal paths at least partially based on a sound speed map corresponding to the detecting transducer;

integrating attenuation along each of the traced acoustic signal paths.

9. The method of claim 8, wherein tracing a plurality of acoustic signal paths includes determining refraction of the acoustic signal paths on the sound speed map corresponding to the detecting transducer.

10. The method of claim 6, wherein transforming at least a portion of the plurality of acoustic signals includes amplifying at least a portion of the plurality of acoustic signals detected by a detecting transducer based on the path average attenuation map for the detecting transducer.

11. The method of claim 10, wherein amplifying at least a portion of the plurality of acoustic signals for a detecting transducer includes multiplying a detected acoustic signal of the plurality of acoustic signals by a factor including a path average attenuation corresponding to the detected acoustic signal.

12. The method of claim 11, wherein multiplying a detected acoustic signal by a factor includes multiplying the detected acoustic signal by an exponent of the corresponding path average attenuation.

13. The method of claim 1, wherein generating a reflection rendering of the volume of tissue includes generating a set of two-dimensional reflection renderings of cross-sections of the volume of tissue.

14. The method of claim 1, wherein generating a reflection rendering includes utilizing a migration algorithm.

15. The method of claim 14, wherein generating a reflection rendering includes utilizing a Kirchhoff migration algorithm.

16. The method of claim 14, further including generating a sound speed rendering of the volume of tissue and generating a plurality of signal variable travel time maps from the sound speed rendering of the volume of tissue, wherein each signal variable travel time map corresponds to a respective transmitting transducer and represents travel time for each detected signal for the respective transmitting transducer.

17. The method of claim 16, wherein generating a reflection rendering of the volume of tissue incorporates the signal variable travel time maps.

18. A method for imaging a volume of tissue within an acoustic coupling medium in a scan region, comprising:

emitting acoustic waveforms from transmitting transducers towards the volume of tissue;

detecting, with detecting transducers, a plurality of acoustic signals derived from acoustic waveforms interacting with the volume of tissue;

generating, from the plurality of acoustic signals, a plurality of path average attenuation maps, wherein each path average attenuation map of the plurality of path average attenuation maps corresponds to a detecting transducer and represents path average attenuation for each of a plurality of acoustic signal paths to the detecting transducer, wherein at least a subset of attenuation coefficients, from the plurality of path average attenuation maps and characterizing the acoustic coupling medium, comprises unequal attenuation coefficients, such that the subset is not defined by a constant attenuation coefficient;

amplifying a first detected acoustic signal of the plurality of acoustic signals based on a first path average attenuation of the plurality of path average attenuation maps, thereby producing a first amplified acoustic signal;

amplifying a second detected acoustic signal of the plurality of acoustic signals based on a second path average attenuation of the plurality of path average attenuation maps, different from the first path average attenuation, thereby producing a second amplified acoustic signal; and generating a reflection rendering of the volume of tissue based on at least the first and second amplified acoustic signals.

19. The method of claim 18, wherein amplifying the first detected acoustic signal includes multiplying the first detected acoustic signal by a factor including an exponent of the first path average attenuation.

20. The method of claim 18, further comprising generating a plurality of signal variable travel time maps from a sound speed rendering of the volume of tissue, wherein each signal variable travel time map corresponds to a respective detecting transducer and represents travel time for each detected signal for the respective detecting transducer.

21. The method of claim 20, wherein generating a rendering of the volume of tissue includes utilizing a Kirchhoff migration algorithm incorporating the plurality of signal variable travel time maps and the amplified acoustic signals.

22. A method for imaging human breast tissue within an acoustic coupling medium in a scan region, comprising:

surrounding the breast tissue with a ring transducer including ultrasound emitters;
emitting ultrasound waveforms towards the breast tissue;
detecting, with detecting transducers, a plurality of acoustic signals derived from ultrasound waveforms interacting with the breast tissue;
generating, from the plurality of acoustic signals, a plurality of variable attenuation maps, wherein each variable attenuation map of the plurality of variable attenuation maps corresponds to a respective detecting transducer and acoustic signals detected by the respective detecting transducer, and wherein each variable attenuation map of the plurality of variable attenuation maps includes a plurality of variable attenuation coefficients mapped to the scan region for the corresponding detecting transducer, wherein at least a subset of attenuation coefficients, from the plurality of variable attenuation maps and characterizing the acoustic coupling medium, comprises unequal attenuation coefficients, such that the subset is not defined by a constant attenuation coefficient;
generating a plurality of path integral attenuation maps from the plurality of variable attenuation maps, wherein each path integral attenuation map of the plurality of path integral attenuation maps corresponds to a detecting transducer and represents path average attenuation for each of a plurality of acoustic signal paths to the detecting transducer;
modifying a first detected acoustic signal of the plurality of acoustic signals based on a first path integral attenuation of the plurality of path integral attenuation maps, thereby producing a first modified acoustic signal;
modifying a second detected acoustic signal of the plurality of acoustic signals based on a second path integral attenuation of the plurality of path integral attenuation maps, different from the first path average attenuation, thereby producing a second modified acoustic signal; and
generating a reflection rendering of the breast tissue based on at least the first and second modified acoustic signals.

\* \* \* \* \*